United States Patent [19]

Morris et al.

[11] Patent Number: 4,489,720

[45] Date of Patent: Dec. 25, 1984

[54] CESAREAN SECTION SURGICAL DRAPE

[75] Inventors: Henrietta K. Morris; Esther R. Lagergren, both of Arlington, Tex.

[73] Assignee: Surgikos, Inc., Arlington, Tex.

[21] Appl. No.: 438,436

[22] Filed: Nov. 2, 1982

[51] Int. Cl.³ .............................................. A61B 19/06
[52] U.S. Cl. ................................................. 128/132 D
[58] Field of Search ...................... 128/132 D, 132 R; 604/322

[56] References Cited

U.S. PATENT DOCUMENTS

| 4,169,472 | 10/1979 | Morris | 128/132 D |
| 4,275,720 | 6/1981 | Wichman | 128/132 D |
| 4,414,968 | 11/1983 | Amin | 128/132 D |

Primary Examiner—Stephen C. Pellegrino
Attorney, Agent, or Firm—Michael Q. Tatlow

[57] ABSTRACT

A surgical drape for use in cesarean section procedures is disclosed. The drape has a fluid collection bag secured to the lower surface of the drape to collect amniotic and other fluids released during the surgery. The fluid collection bag is maintained in an open position by a moldable strip at the opening of the bag. An adhesive at the opening of the bag seals the bag after use.

7 Claims, 6 Drawing Figures

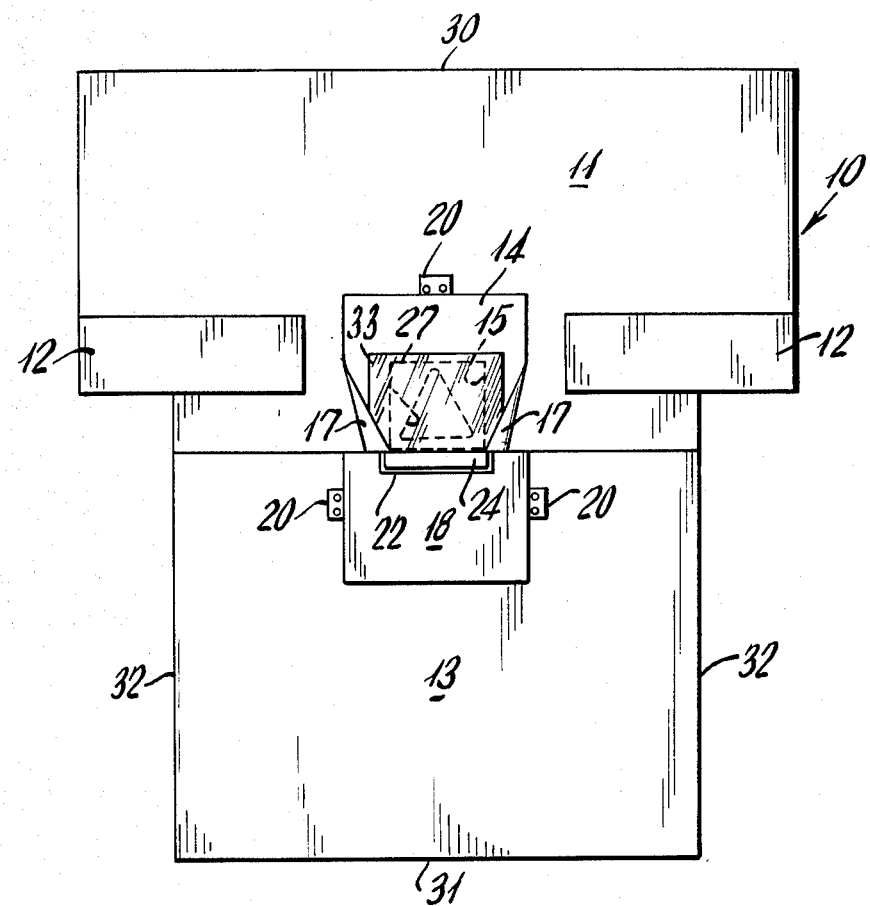
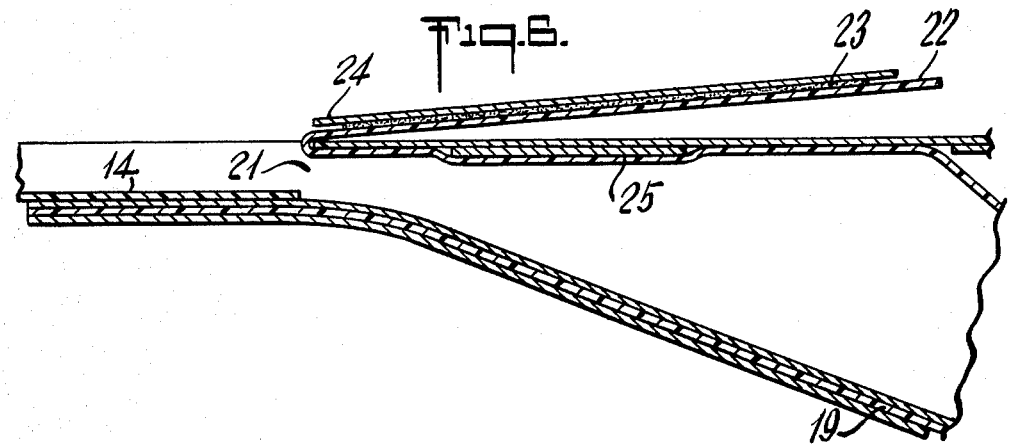

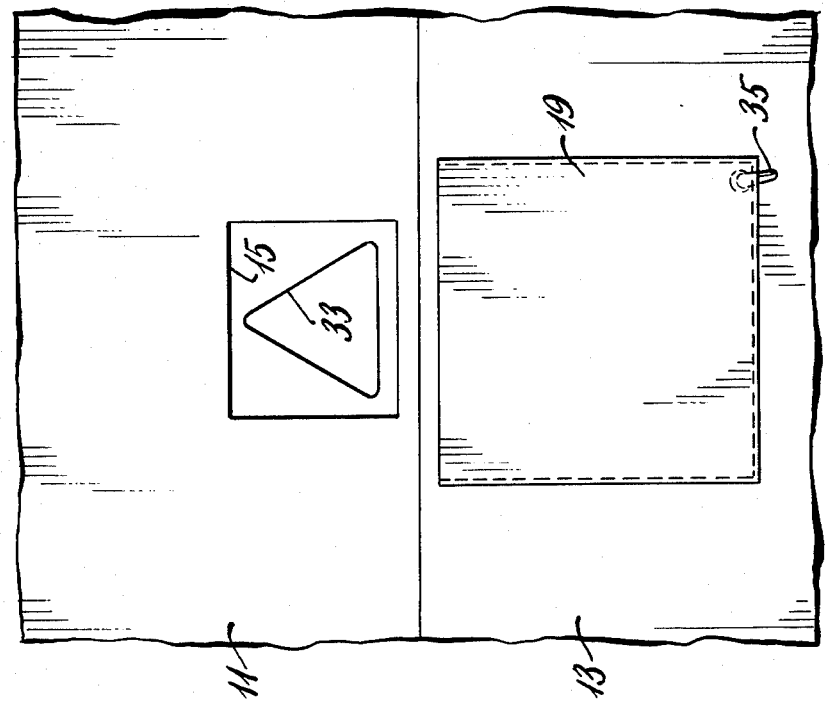
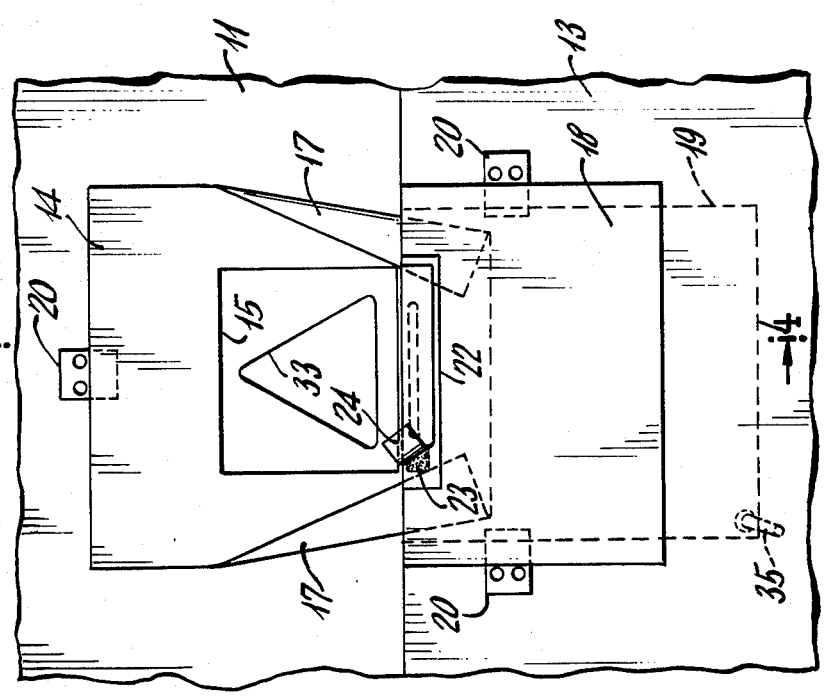

CESAREAN SECTION SURGICAL DRAPE

FIELD OF THE INVENTION

The present invention relates to surgical drapes, and more particularly surgical drapes which are disposable and which are particularly suited for use in the performance of a cesarean section.

PRIOR ART

Surgical drapes are customarily used in an operating room to protect the site of the operation from possible contamination from bacteria which can be found on other portions of the patient's body and which may be airborne or conveyed to the surgical patient by the operating room staff. The patient is essentially isolated from the operating room environment and the operating room staff by the placement of surgical drapes which cover the patient's body other than that portion of the body which is the site of the surgical procedure.

Surgical drapes are also used in a delivery room when a woman is giving birth to a child. In normal delivery, the surgical drapes cover the upper portion of the woman's body as well as the legs, which are usually placed in stirrups in an elevated position slightly above the patient's body.

If the delivery of the child is by cesarean section, the drapes that are employed for normal deliveries are not appropriate. In a cesarean section delivery, the patient is in a flat position or rolled toward the left side and their legs are not elevated. Drapes that have previously been used for cesarean section procedures include the laparotomy drapes which are used for abdominal surgery. Although these drapes are adequate for protecting the patient from possible bacteria contamination, they do not provide for the handling of the significant amounts of amniotic fluid and other body fluids that are commonly released during the cesarean section procedure.

Surgical drapes which provide some mechanism for the direction of body fluids have previously been known. For example, U.S. Pat. No. 3,791,382 discloses surgical drape constructions which provide a pocket on the outer surface of the drape to receive fluid runoff from the site of the surgical procedure. U.S. Pat. No. 4,076,017 and U.S. Pat. No. 4,105,019 disclose surgical drapes specifically directed to the problem of postpartum fluid control. These patents disclose a pocket formed on the outer surface of the surgical drape by folding an edge of a nonabsorbent sheet upon itself and sealing it together. U.S. Pat. No. 4,169,472 discloses a surgical drape which includes an impervious bag used for collecting liquids and other fluids which may be present during the operating procedure. This patent is particularly directed to surgical drapes which are used in surgical procedures involving a patient's head. The bag disclosed in this patent is on the outer surface of the drape, that is, that portion of the drape which is away from the patient's body during the surgical procedure.

Although all of the above-mentioned drapes disclose some provision for the collection of body fluids, the construction of the drapes are inappropriate for a cesarean section surgical procedure. The normal use of the drapes disclosed in the prior art presumes that the fluid will flow away from the site of the surgical procedure, across the upper surface of the drape, to the pocket which is on the upper surface of the surgical drape but below the site of the surgical procedure. In the cesarean section procedure, the patient is substantially in a flat position or rolled toward the left side and, therefore, the surgical drapes with fluid direction means on the outer surface of the drape are not sufficient to collect fluids which are present during the cesarean section procedure.

SUMMARY OF THE INVENTION

The present invention relates to a surgical drape which is disposable and which is particularly suited for use in a cesarean section procedure. The disposable drape of the present invention is constructed so that it may be used to collect fluids even when the patient is in a generally flat or horizontal position. The present drape includes a fluid direction system which will direct amniotic fluids from the surface of the drape, through an opening in the drape, to a collection bag which is disposed on the under or lower surface of the drape. The collection bag may be readily placed between the patient's legs when the patient is in a flat or rolled position. The drape also includes a mechanism to maintain the opening to the fluid collection bag in an open position during the surgical procedure, and it also provides a sealing system to seal the bag containing such body fluids after the surgical procedure has been completed.

Other details of the present invention will be readily apparent to one skilled in the art from the description of the invention which follows.

BRIEF DESCRIPTION OF THE DRAWINGS

FIG. 1 is a top plan view of the surgical drape of the present invention.

FIG. 2 is a fragmentary top plan view of the fenestration area of the drape.

FIG. 3 is a fragmentary bottom plan view of the area of the drape shown in FIG. 2.

FIG. 6 is a detailed cross-sectional view of the opening to the collection bag in the drape.

Detailed Description of the Invention

Figures 4, 5:
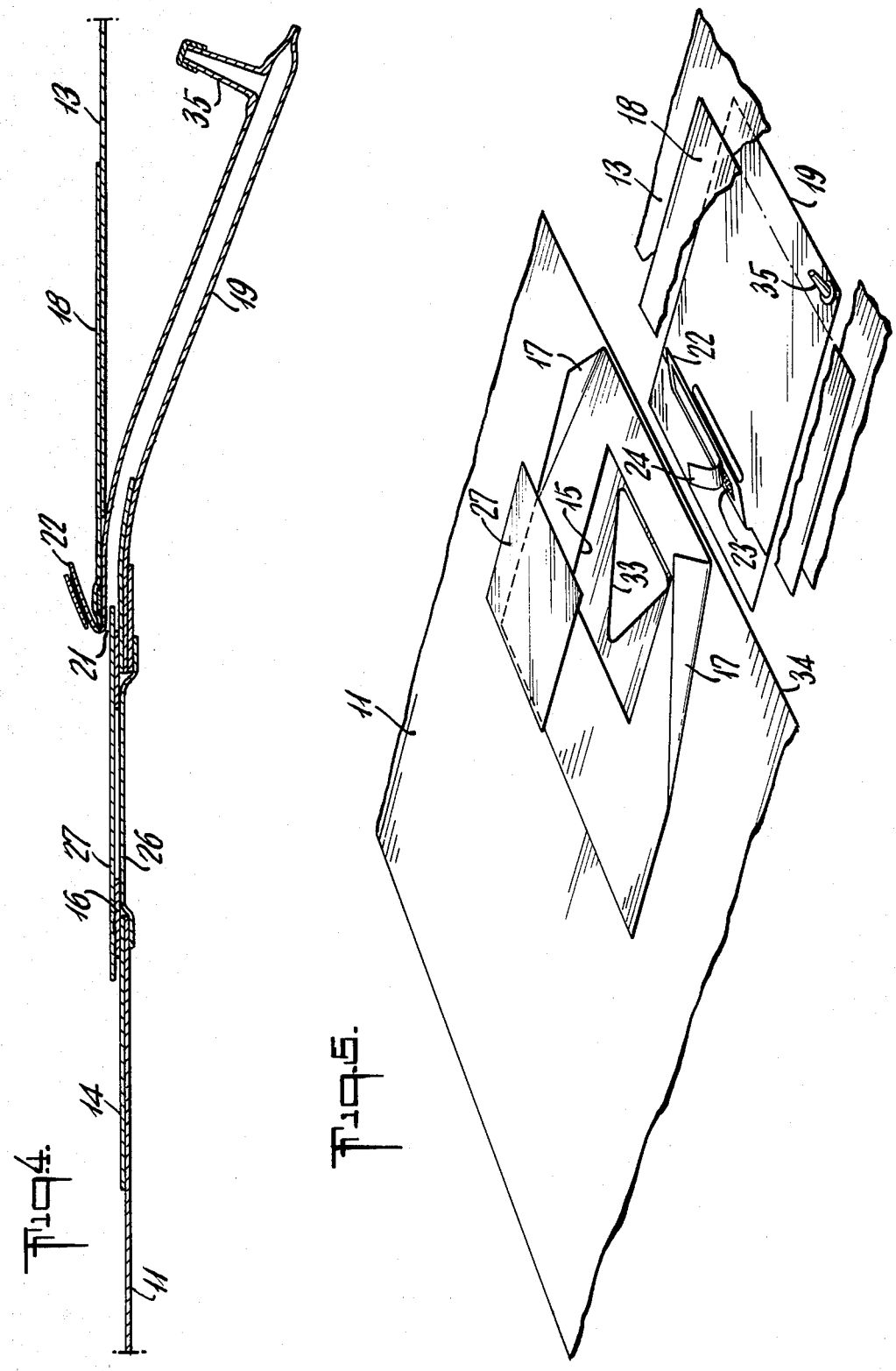
FIG. 4 is a cross-sectional view of the drape taken along lines 4—4 of FIG. 2.
FIG. 5 is an exploded fragmentary view of the drape.

The surgical drape of the present invention is generally shown in FIG. 1. The drape 10 has a top edge 30, a bottom edge 31 and two side edges 32. FIG. 1 shows the upper surface of the drape, which is that surface which is away from the patient's body. The lower surface of the drape is in contact with the patient's body. The surgical drape shown in FIG. 1 has an upper portion 11 which may be transverse to the length of the drape and which forms a cross or T-portion of the drape. When the drape is in use, the upper portion is placed toward the head of the patient. At the bottom edge of the upper portion of the drape there may be flaps 12 which function to cover an arm board, if an arm board is used in the surgical procedure. The surgical drape of the present invention may also be fabricated as a large rectangular sheet with a constant width rather than a T-shaped sheet.

The lower portion of the drape 13 is that portion of the drape which is placed toward the feet of the patient. The upper portion 11 and the attached lower section 13 of the drape will hereinafter be referred to as the main sheet of the drape. On the upper surface of the drape, there is a first reinforcement panel 14 which extends from the upper portion 11 of the drape to the lower portion of the drape. This reinforcement panel is generally made with an impervious film covered with an absorbent material. The impervious film is in contact with the upper surface of the main portion of the surgical drape, and the absorbent surface overlies the film and is the upper surface of the drape. There is an opening 15 in the drape, which in FIG. 2 is shown to be rectangular in shape. There is an adhesively-coated plastic film 16 over the opening and a triangular fenestration 33 in the film. It should be understood that the fenestration may be any desirable configuration, the triangular configuration being particularly useful in cesarean section procedures. The adhesive coating on the film faces the patient and is covered before use with a releasable paper. The nonadhesive surface of the film is also covered with a removable paper insert 27 to maintain the sterility of the film during the placement of the drape on the patient.

The first reinforcement panel 14 is secured to the main surface of the drape by lines of adhesive which are spaced inwardly from the side edges of the reinforcement panel. This provides a flap of unsecured reinforcement material which can be folded to provide fluid direction flaps, as indicated at 17 in FIG. 1. The top portion of the flap may also be used to secure surgical instruments, tubing and wires to the upper surface of the drape by means of clamps.

There is a second reinforcement panel 18 spaced below, that is, toward the bottom edge of the drape, from the first reinforcement panel. The second reinforcement panel is also constructed of a fluid-impervious plastic film with an absorbent upper surface. The second reinforcement panel is adhesively secured to the upper surface of the lower portion 13 of the drape. Between the first reinforcement panel and the second reinforcement panel, there is an opening through the main sheet of the drape. There is a fluid collection bag 19 on the lower surface of the drape. The opening in the bag is secured to the edges of the opening in the drape into which the flaps 17 are directed. The fluid collection bag is secured to the surface of the drape only at its open end, as is shown in FIGS. 4 and 6. The lower or closed end of the fluid collection bag is free of the drape and may readily be placed between the patient's legs so that the fluid collected during the surgical procedure will be collected away from the upper surface of the drape and will not interfere with the surgical procedure.

The opening 21 may be formed by cutting or slitting the lower portion 13 of the main sheet of may be formed by the selected glueing of drape fabrics as shown in FIG. 5. In FIG. 5, the top portion 11 of the main sheet extends to the bottom of the first reinforcement panel 14. The lower surface of the fluid collection bag 19 is glued to the upper surface of sheet 11. The lower portion 13 of the drape is then glued to the top portion of the sheet 11 and to the upper surface of the bag 19 at the opening of the bag. The reinforcement panel is then glued to the sheet 11 and the flaps 17 inserted into the opening 21 of the bag 19. The second reinforcement panel 18 is then glued to the drape. The top edge of the second reinforcement panel 18 extends onto the bottom edge 34 of the top portion 11 of the main sheet. There may be a drainage tube 35 in the lower, closed end of the bag 19 to drain excess fluid from the bag 19.

The upper, top edge of the fluid collection bag which is on the upper surface of the drape forms a flap 22 and has an adhesive, preferably a double-faced adhesive tape 23 on its surface. There is a release sheet 24 over the outer surface of the tape. This flap 22 is folded away from the opening 21. The purpose of the adhesive surface is to allow the collection bag to be sealed after the completion of the surgical procedure so that the fluid will not escape from the bag as the drape is being removed from the patient.

There is a thin, moldable metal or plastic strip 25 in the drape at the opening or mouth of the bag as shown in FIGS. 2, 4 and 6. The purpose of the strip, which is moldable and is capable of being bent and being maintained in a fixed configuration, is to provide better direction of the fluid into the bag during the surgical procedure and to prevent the bag from being inadvertently closed during the surgical procedure.

The edges of the reinforcement panels 14 and 18 may also contain tubing or cord holders 20 which are useful to secure suction tubing or cautery wires to the upper surface of the drape during the procedure.

The drape is folded into a compact size to allow the drape to be aseptically placed in position on the patient. The drape is preferably folded so that the incise film 16 is on the outer surface of the folded drape. When placing the drape on the patient, the release sheet 26 is removed from the adhesive surface of the film 16, and the film is secured to the skin of the patient over the operative site. The drape is then unfolded and spread over the patient's body. After the drape is unfolded, the paper insert 27, covering the upper surface of the film 16, is removed and discarded. The initial surgical incision is made through the fenestration 33 in the film. The metal strip 25 is then bent in an appropriate shape to insure the opening 21 is maintained in communication with the fluid collection bag 19. The bag 19 may be conveniently placed between the patient's legs, out of the way of the surgical staff. Any fluid from the site of the incision is directed by the flaps 17 through the opening 21 in the drape and into the fluid collection bag 19. When the surgical incision is to be closed, the release sheet 24 on the flap 22 of the bag is removed, and the flap 22 is secured to the upper surface of the drape, sealing the fluid collection bag.

We claim:

1. A surgical drape having a top edge and a bottom edge and two opposing side edges, and an upper surface and a lower surface, a fenestration through the drape in a centrally located area of the drape, a reinforcement panel around the fenestration, said reinforcement panel being attached to the upper surface of the drape along lines spaced inwardly from the side edges of the reinforcement panel to provide flexible flaps on the side edges of said reinforcement panel, an opening through the drape between the fenestration and the bottom edge of the drape, a fluidimpervious bag attached to the lower surface of the drape, an opening in said bag secured to the edges of the opening in the drape, said flexible flaps on said reinforcement panel being folded so that the lower edges of said flaps extend into the impervious bag, a second reinforcement panel which extends to the opening in the drape and over the flaps.

2. The surgical drape of claim 1 including an adhesive on the upper surface of the fluid impervious bag to seal the bag after use.

3. The surgical drape of claim 1 including a moldable strip positioned at the mouth of the impervious bag and across the width of the opening to allow the bag to be maintained in an open position.

4. The surgical drape of claim 1 in which there is a drainage tube in the impervious bag.

5. A surgical drape comprising a main sheet for placement on the patient's body, said main sheet having an upper surface, a lower surface, a top edge, a bottom edge, two opposed side edges and an upper portion and a lower portion;
  an opening in said main sheet between said upper portion and said lower portion;
  a fluid collection bag having an open end in communication with the opening in said main sheet and being secured on the lower surface of said main sheet;
  a reinforcement panel having a top edge, a bottom edge and two opposed side edges affixed to the upper surface of the upper portion of the main sheet along lines spaced inward from the side edges of the panel to provide flexible flaps in said panel;
  the lower ends of said flaps being folded and positioned through said opening in said main sheet and into the open end of said fluid collection bag to direct fluid from the upper surface of said drape into said fluid collection bag;
  a second reinforcement panel on the upper surface of the lower portion of the main sheet, said second reinforcement being at the lower edge of said opening and extending over the flaps of said first reinforcement panel.

6. The surgical drape of claim 5 including a moldable strip positioned at the mouth of said fluid collection bag adaptable to maintain the bag in an open position and also including an adhesive seal at the mouth of said fluid collection bag to seal the bag after use.

7. The surgical drape of claim 6 including a drainage tube in said impervious bag.

* * * * *